United States Patent [19]

Steinmetz et al.

[11] Patent Number: 4,902,827
[45] Date of Patent: Feb. 20, 1990

[54] PROCESS FOR THE PREPARATION OF ADIPIC ACID

[75] Inventors: Guy R. Steinmetz; Norma L. Lafferty; Charles E. Sumner, Jr., all of Kingsport, Tenn.

[73] Assignee: Eastman Kodak Company, Rochester, N.Y.

[21] Appl. No.: 189,933

[22] Filed: May 3, 1988

[51] Int. Cl.$^4$ .................. C07C 51/31; C07C 55/14
[52] U.S. Cl. ..................... 562/543; 562/528; 562/529; 562/530; 562/538
[58] Field of Search ............... 562/543, 528, 529, 530, 562/538

[56] References Cited

U.S. PATENT DOCUMENTS

| | | | |
|---|---|---|---|
| 3,231,608 | 1/1966 | Kollar | 562/543 |
| 3,390,174 | 6/1968 | Schulz et al. | 562/543 |
| 3,649,685 | 3/1972 | Ishimoto et al. | 562/543 |
| 3,987,100 | 10/1976 | Barnette et al. | 562/543 |
| 4,032,569 | 6/1977 | Omepchenke et al. | 562/543 |
| 4,098,817 | 7/1978 | Barone | 562/543 |
| 4,263,453 | 4/1981 | Schulz et al. | 562/543 |

FOREIGN PATENT DOCUMENTS

| | | | |
|---|---|---|---|
| 50087 | 12/1972 | Japan | 562/543 |
| 116415 | 9/1975 | Japan | 562/543 |

OTHER PUBLICATIONS

K. Tanaka, Adipic Acid in One Step, Chemtech, Sep. 1974, p. 555.
K. Tanaka, Adipic Acid by Single Stage, Hydrocarbon Processing, Nov. 1974, p. 114.

*Primary Examiner*—Vivian Garner
*Attorney, Agent, or Firm*—J. Frederick Thomsen; William P. Heath, Jr.

[57] ABSTRACT

Disclosed is an improved process for the preparation of adipic acid by the air oxidation of cyclohexane in the presence of acetic acid and a catalyst system comprising cobalt and zirconium and/or hafnium.

4 Claims, No Drawings

PROCESS FOR THE PREPARATION OF ADIPIC ACID

This invention concerns a novel and improved process for the one-step preparation of adipic acid by the oxidation of cyclohexane.

The preparation of adipic acid by a one-step or one-stage oxidation of cyclohexane has been investigated extensively. Two 1974 publications by K Tanaka appearing in Hydrocarbon Processing, November, 1974, p. 114 and in Chemtech, September, 1974, p. 555 are representative of the prior art. The primary focus of previous attempts to oxidize cyclohexane in one step to adipic acid has been on the use of cobalt as the catalyst. Tanaka observed that selectivity to adipic acid is maximized by the use of lower temperatures, e.g. from 80°-100° C. or moderately higher, and that at some point between 100° and 130° C. selectivity decreased markedly and reaction rate also decreased at temperatures above 130° C. Tanaka also described the use of various promoters to convert the cobalt from the cobaltous (+2) state to the catalytically-active cobaltic (+3) state. Acetaldehyde was used in most of the work reported. Acetaldehyde, like the other promoters mentioned by Tanaka, is rapidly consumed during the oxidation of cyclohexane and thus must be continuously fed to the oxidizer to maintain the activity of the cobalt catalyst. Since the consumption of the acetaldehyde results in the formation of acetic acid, the use of acetaldehyde as a promoter in the cobalt-catalyzed oxidation of cyclohexane results in the net production of acetic acid. However, this coproduction method is a very economically unattractive means for the production of acetic acid.

U.S. Pat. No. 3,649,685 discloses the air oxidation of cyclohexane to adipic acid using a catalyst system composed of an organic carboxylate of cobalt and a bromine compound. Due to its corrosive characteristics, the presence of bromine requires the use of halogen-resistant materials of construction and thus increases substantially the cost production facilities.

We have discovered that the use of zirconium, hafnium or mixtures thereof in combination with conventional cobalt catalysts in the air oxidation of cyclohexane to adipic acid improves reaction rate and/or selectivity to adipic acid. Thus, our invention provides a novel and improved process for the production of adipic acid by the air oxidation of cyclohexane in the presence of acetic acid and a catalytically effective amount of a soluble cobalt compound in combination with a soluble zirconium and/or hafnium compound. The use of zirconium and/or hafnium as a promoter in the cobalt catalyzed oxidation of cyclohexane is advantageous in that it is not consumed in the reaction and therefore can be reused or recycled, and its presence does not require the use of expensive halogen-resistant materials of construction.

The concentration of the catalyst components in the oxidation medium, i.e., acetic acid, can be varied substantially depending on several factors such as, for example, the particular oxidation temperature and pressure being used, the mode of operation, the oxidation rate desired, the amount of cyclohexane present or the rate at which it is fed to the oxidation zone, the presence of additional catalyst components, i.e., in addition to cobalt, zirconium and/or hafnium, etc. Typically, the concentration of cobalt [Co] in the oxidation medium may be in the range of about 0.001 to about 10.0 weight percent based on the weight of the acetic acid solvent. However, the process normally will be carried out using a cobalt cencentration (same basis) in the range of about 0.005 to 1.00, preferably about 0.01 to 0.50 weight percent. The amount of zirconium or hafnium that may be used effectively in our process is that amount which will give a Zr:Co, Hf:Co or Zr+Hf:Co atomic ratio in the range of about 0.001 to 1,000, preferably in the range of about 0.01 to 10.0.

The particular soluble cobalt compound that is charged initially to the reaction zone or is added to the oxidation process to make up for cobalt lost in product isolation is not critical. For example, the cobalt may be supplied as cobalt hydrate or in the form of various salts such as a halide, nitrate or carboxylate, e.g., acetate, propionate, naphthanoate, etc. The form of the soluble zirconium and hafnium compound used likewise is not important. Examples of suitable compounds include zirconium acetate, zirconium naphthenate, zirconium tetrachloride, zirconium sulfate, hafnium sulfate, etc.

The oxidation process provided by our invention is carried out under adipic acid-forming conditions of pressure and temperature. Since the pressure and temperature are, to some extent, interdependent, each can be varied considerably. Typically, the process can be carried out at a pressure (total) in the range of about 2 to 100 bar and a temperature in the range of about 80° to 160° C. Normally, good to excellent results, in terms of oxidation rate and selectivity to adipic acid, can be realized by conducting the process at a pressure in the range of about 2 to 30 bar and at a temperature in the range of about 90° to 120° C.

The amount of cyclohexane present in the oxidizer or the amount added during continuous operation can be varied substantially depending on numerous factors such as the air flow through the oxidizer, the conditions of pressure and temperature and the rate at which the cyclohexane is being oxidized. While the oxidizing gas has been referred to herein as air, any gas containing molecular oxygen may be used. For example, oxygen enriched air may be employed to permit the use of lower oxidation pressures. In the continuous operation of the process, a minor amount of acetaldehyde may be fed, either continuously or intermittently, with the cyclohexane feed and/or acetic acid-catalyst recycle to replace acetic acid which is decomposed in the oxidizer.

The cyclohexane oxidation process may be carried out as a batch or semi-continuous process wherein cyclohexane, acetic acid and the catalyst components are charged to an agitated pressure vessel which is then heated to the desired oxidation temperature and pressurized with an oxygen-containing gas such as air or oxygen-enriched air. After all or substantially all of the cyclohexane has been converted to other compounds, the reactor contents are discharged and the adipic acid is separated from the acetic acid-catalyst component solution which also contains intermediate oxidation products, e.g., cyclohexanol and cyclohexanone, and by-products, e.g., succinic and glutaric acids.

The preferred mode of operation is a continuous process using, for example, a columnar reactor wherein an oxygen-containing gas is fed by means of a sparger at the base of the reactor and cyclohexane (optionally containing cyclohexanol and/or cyclohexanone) and acetic acid containing the catalyst components are fed at a point or points intermediate the top and bottom of the reactor. Crude oxidizer product solution is removed continuously from the bottom of the reactor. Adipic acid and by-products are removed, and acetic acid-catalyst solution is recycled continuously to the reactor. Since the oxidation reaction is exothermic, the temperature within the reactor may be controlled by removing vapor from the top of the reactor and returning acetic acid and other condensible materials to the reactor.

Our novel process is further illustrated by the following examples.

Examples 1 and 2 and Control or Comparative Examples 1–4 were carried out in a 600-mL, stirred glass autoclave equipped with an overhead stirrer, reflux condenser, and lines for liquid and gas feeds. Exiting gas flow was measured with a wet test meter. The autoclave was charged with the following materials:

Cobaltous acetate, $Co(OAc)_2 \cdot 4H_2O$, 5.0 g, 0.0201 mol;
Zirconium acetate, $ZrO(OAc)_2 \cdot xH_2O$, 2.63 g, 0.0053 mol, Examples 1 and 2 and Control Example 4;
Peracetic acid, 1.0 mL 30% peracetic acid, to activate the catalyst by converting the cobalt to the cobaltic state;
Cyclohexane, 34.0 g, 0.404 mol;
Acetic acid, 200 mL except in Control Examples 3 and 4 in which 140 mL were charged initially and a mixture of acetaldehyde and acetic acid in a volume proportion of 3:22 was fed continuously at a rate of 12 mL/hour over the course of the oxidation period begining with the achievement of the oxidation temperature.

The autoclave was pressurized to 50 psig (3.45 bar) with air flow set on 50 (6.4 scfh, 181 L/hour). The reactor then was heated to the desired temperature (100° to 110° C.) marking the beginning of the oxidation period. Material condensed from the off-gas was returned to the reactor. At the end of five hours, the air flow was stopped and the autoclave was vented and cooled.

Examples 3–5 and Control Examples 5–13 were carried out in a 2-liter, stirred autoclave constructed of Hastelloy C alloy metal. These oxidation reactions were carried out in substantially the same manner as described above except for the following changes: (1) air and nitrogen were fed at 6 scfh (170 L/hour) to maintain the off-gas at 8 or less percent oxygen, (2) total pressure was 300 psig (20.68 bar) and (3) the materials charged were:

Cobaltous acetate, 15.0 g, 0.0602 mol;
Zirconium Acetate, 7.9 g, 0.0160 mol,

Examples 3–5 and Control Examples 11–13;
Peracetic acid, 3.0 mL 30% peracetic acid;
Cyclohexane, 102.0 g, 1.21 mol;
Acetic acid, 600 mL except in Control Examples 8–13 in which 510 mL were charged initially and a mixture containing varying amounts of acetaldehyde and acetic acid were fed continuously at a rate of 18 mL/hour. The volume proportion of acetaldehyde/acetic acid in the mixtures were: Control Examples 8 and 11: 2/17; Control Examples 9 and 12: 4/15; Control Examples 10 and 13: 8/11.

The following Table shows the amounts (millimoles) of adipic acid and co-products succinic and glutaric acids produced and the oxidation temperature (°C.) employed in each of the examples described hereinabove. Also set forth in the Table are the yield of adipic acid for each example which is the amount of adipic acid produced as a mole percent of the cyclohexane charged and the selectivity of adipic acid which is given as a percent moles of adipic acid produced per total moles of succinic (SA), glutaric (GA) and adipic (AA) acids produced. The moles of acids produced in each example were determined by liquid chromatography analysis of a sample of the reaction mixture obtained at the conclusion of each example. The control examples are indicated by a C.

TABLE

| Ex. | Temp | SA | GA | AA | Yield | Selectivity |
|-----|------|------|------|-------|-------|-------------|
| C1  | 100  | —    | 0.28 | 4.3   | 1.1   | 93.5        |
| 1   | 100  | 3.99 | 4.86 | 15.0  | 3.7   | 62.8        |
| C2  | 110  | 2.10 | 3.28 | 15.3  | 3.8   | 73.9        |
| 2   | 110  | 7.64 | 9.91 | 56.1  | 13.9  | 76.2        |
| C3  | 110  | 18.2 | 15.4 | 44.8  | 11.1  | 57.1        |
| C4  | 110  | 21.8 | 18.4 | 50.4  | 12.5  | 55.6        |
| C5  | 90   | 13.7 | 16.3 | 143.0 | 11.8  | 82.7        |
| 3   | 90   | 29.4 | 33.7 | 271.0 | 22.4  | 81.1        |
| C6  | 100  | 23.1 | 28.2 | 200.0 | 16.5  | 79.6        |
| 4   | 100  | 34.7 | 42.7 | 263.0 | 21.7  | 77.3        |
| C7  | 110  | 33.5 | 39.7 | 248.0 | 20.4  | 77.2        |
| 5   | 110  | 38.1 | 49.7 | 256.0 | 21.1  | 74.5        |
| C8  | 90   | 33.4 | 33.9 | 262.0 | 21.6  | 79.6        |
| C9  | 90   | 46.5 | 48.6 | 298.0 | 24.6  | 75.8        |
| C10 | 90   | 42.5 | 43.4 | 318.0 | 26.2  | 78.7        |
| C11 | 90   | 44.9 | 45.1 | 305.0 | 25.2  | 77.2        |
| C12 | 90   | 43.4 | 44.8 | 298.0 | 25.2  | 77.2        |
| C13 | 90   | 79.2 | 69.9 | 325.0 | 26.8  | 68.6        |

From the data set forth in the Table, it is readily apparent for the low pressure runs that increasing the temperature from 100° C. to 110° C. results in higher yields. However, the presence of zirconium results in equal yields at lower temperatures (cf. Examples 1 and C2) or higher yields at equivalent temperatures (cf. Examples 2 and C2). Addition of acetaldehyde results in higher yields but has no significant effect on the cobalt-zirconium catalyst system. The results obtained from the high pressure oxidations are consistent with the low pressure results and show that the presence of zirconium results in higher yields at lower temperatures when compared to the runs carried out with only cobalt and approximately the same yields when compared to the cobalt-acetaldehyde runs. The data also establish that the presence of zirconium results in a beneficial effect under a number of different operating conditions.

While the catalyst system of our novel process has been described hereinabove as containing cobalt in combination with zirconium and/or hafnium, it will be readily apparent to those skilled in the art that additional catalytically effective components may be employed. Thus, manganese and bromine compounds may be used in addition to, or as a partial replacement of, the cobalt component in the above-described process.

While the invention has been described in detail with particular reference to preferred embodiments thereof, it will be understood that variations and modifications can be effected within the spirit and scope of the invention.

We claim:

1. Process for the preparation of adipic acid which comprises contacting cyclohexane with air in the presence of acetic acid and a catalytic amount of a combination of a soluble cobalt compound and a soluble zirconium and/or hafnium compound at a temperature of about 80° to 160° C. and a pressure of about 2 to 100 bar, wherein the atomic ratio of Zr:Co, Hf:Co or Zr+Hf:Co is about 0.001 to 1,000.

2. Process according to claim 1 wherein cyclohexane is contacted with air in the presence of acetic acid containing about 0.005 to 1.00 weight percent cobalt based on the weight of acetic acid and zirconium or hafnium in an amount which gives a cobalt to zirconium or hafnium atomic ratio of about 0.01 to 10.0.

3. Process according to claim 1 for the preparation of adipic acid which comprises contacting cyclohexane with air at a temperature of about 80° to 160° C. and a pressure of about 2 to 100 bar in the presence of acetic acid containing about 0.01 to 0.50 weight percent cobalt based on the weight of the acetic acid and zirconium in an amount which gives a cobalt to zirconium atomic ratio of about 0.01 to 10.0.

4. Process for the preparation of adipic acid which comprises contacting cyclohexane with air at a temperature of about 90° to 120° C. and a pressure of about 2 to 30 bar in the presence of acetic acid containing a soluble cobalt compound in an amount which gives a cobalt concentration of about 0.01 to 0.50 weight percent based on the weight of the acetic acid and a soluble zirconium compound in an amount which gives a Zr:Co atomic ratio of about 0.01 to 10.0.

* * * * *